United States Patent [19]
Heller et al.

[11] Patent Number: 6,017,349
[45] Date of Patent: Jan. 25, 2000

[54] TRANSPORT AND PROCESSING APPARATUS FOR A TWO-COMPONENT MATERIAL

[75] Inventors: Mathias Heller, Winterthur; Anton Spaltenstein, Kloten; Werner Fritz Dubach, Maur, all of Switzerland

[73] Assignee: Sulzer Orthopaedie, AG, Baar, Switzerland

[21] Appl. No.: 09/082,849

[22] Filed: May 21, 1998

[30] Foreign Application Priority Data

Jun. 5, 1997 [EP] European Pat. Off. .............. 97810352

[51] Int. Cl.$^7$ ..................................................... A61B 17/56
[52] U.S. Cl. ................................................. 606/92; 606/93
[58] Field of Search ................................. 606/92, 93, 94, 606/95, 86; 604/82, 83, 84, 85, 86, 87, 88, 92, 191

[56] References Cited

U.S. PATENT DOCUMENTS

| | | | |
|---|---|---|---|
| 4,751,921 | 6/1988 | Park | 606/93 |
| 5,681,317 | 10/1997 | Caldarise | 606/93 |

FOREIGN PATENT DOCUMENTS 0 397 589 A1  11/1990  European Pat. Off. .
WO 87/05492  9/1987  WIPO .

*Primary Examiner*—Michael Buiz
*Assistant Examiner*—William Lewis
*Attorney, Agent, or Firm*—Townsend and Townsend and Crew LLP

[57] ABSTRACT

A transport and processing apparatus for a two-component material, in particular for bone cement, has a liquid component (1) and a powder component (2) which are separated by a membrane (3) and each occupy a transport chamber (4, 5) in a closeable container (6, 7) which has an expulsion piston (8) at one end and an opening (9) for the expulsion of mixed two-component material at the opposite end. The transport chamber (4) for the liquid component has a ring shape and a central aperture (34) for expelling the mixed two-component material through the aperture (34). The membrane is destroyed by a relative movement between the transport chamber for the liquid component (1) and a solid body (12, 17) enclosed in the container in order to effect a flow of the liquid component (1) into the transport chamber (5) for the powder component (2) and to enable the mixing with a mixing piston (11).

19 Claims, 9 Drawing Sheets

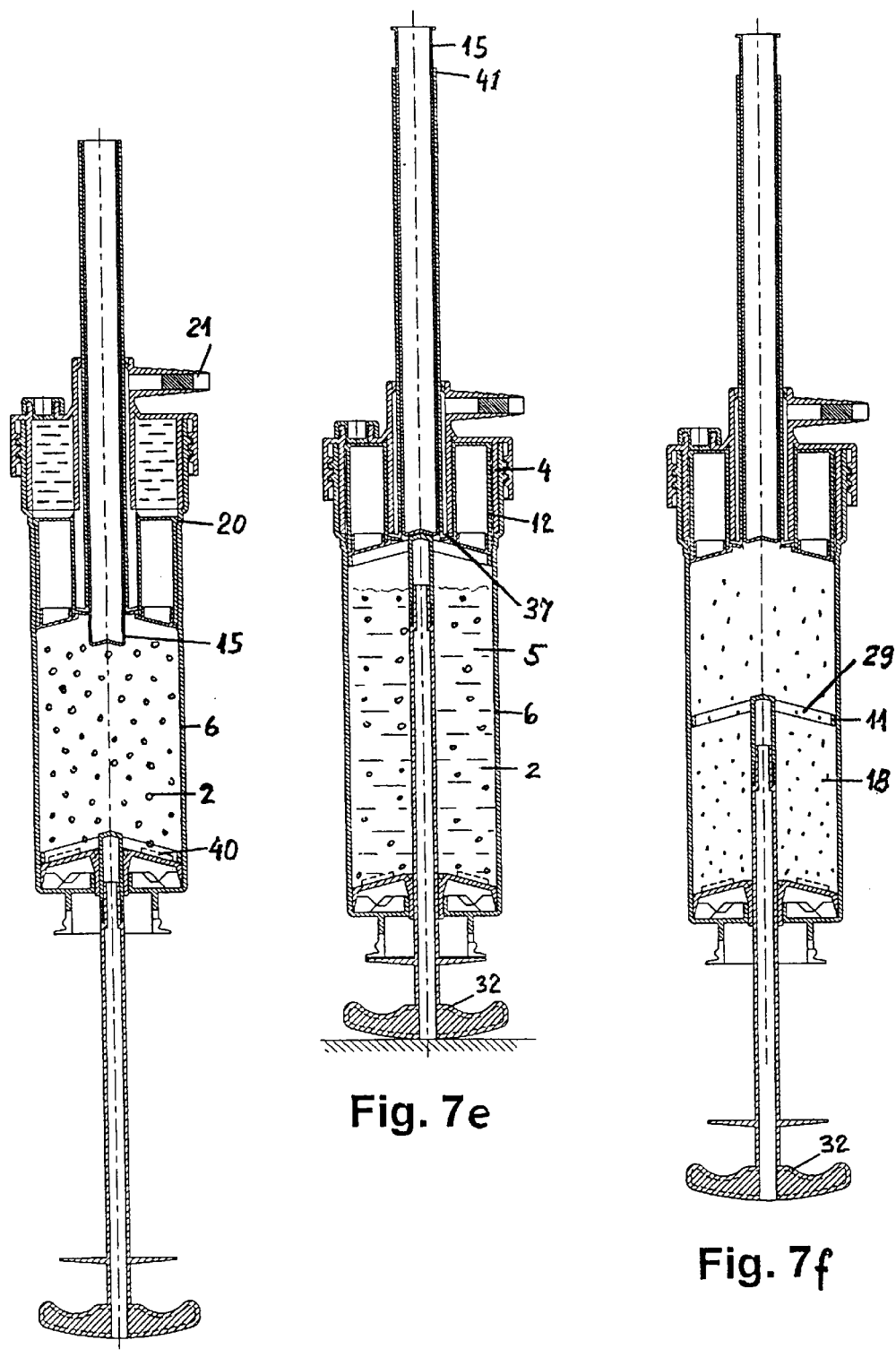

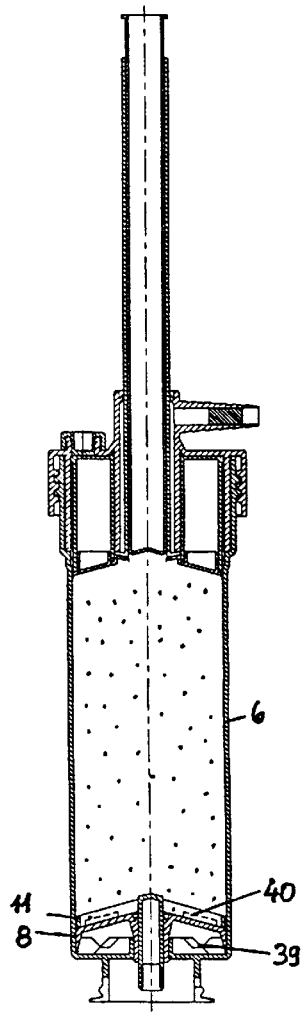
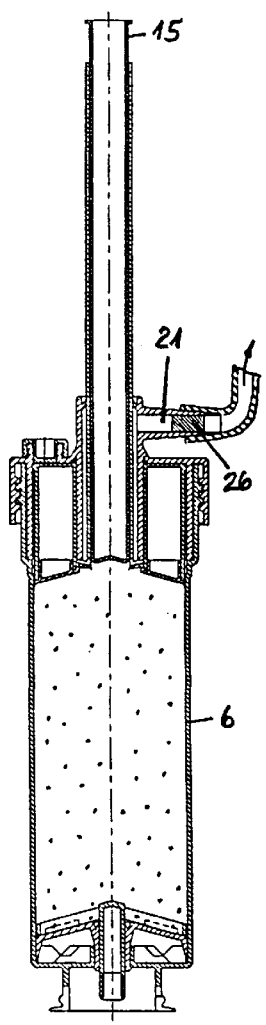
Fig. 7h
Fig. 7i
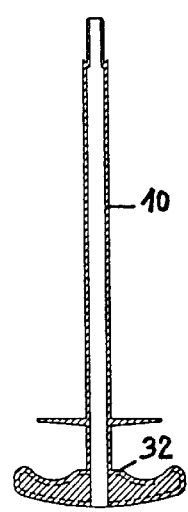
Fig. 7g

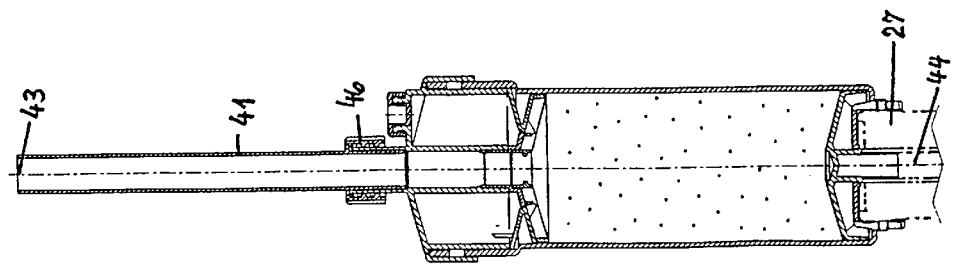
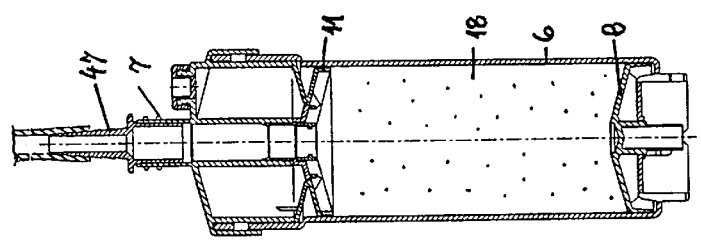
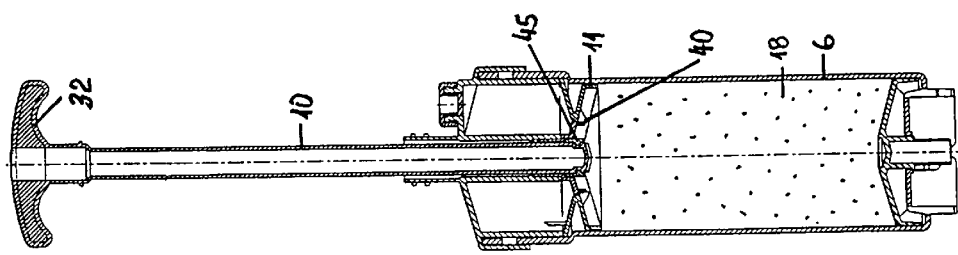
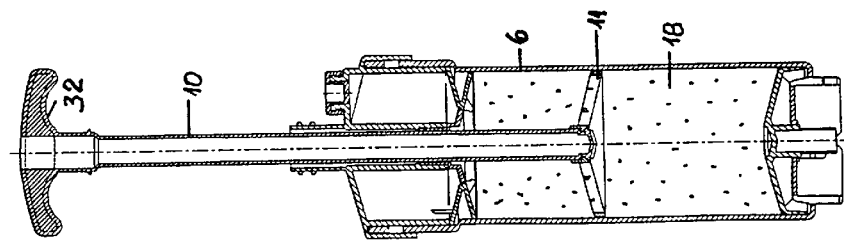
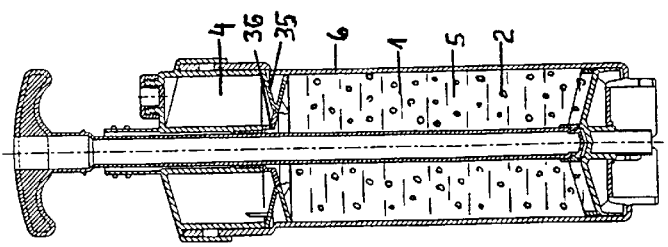

TRANSPORT AND PROCESSING APPARATUS FOR A TWO-COMPONENT MATERIAL

BACKGROUND OF THE INVENTION

The invention relates to a transport and processing apparatus for a two-component material, in particular for bone cement, with a liquid component and a powder component which are separated by a membrane and which each occupy a transport chamber in a closeable container which has an expulsion piston at one end and an opening for the expulsion of mixed two-component material at the opposite end and which encloses a perforated mixing piston.

An apparatus of this kind is shown in EP-A-0 692 229. A separating piston, which separates the powdery region from the region of the liquid component, is arranged between an expulsion piston and a mixing piston. The mixing cylinder is assembled of two separate transport cylinders which can be assembled via a rapid coupling. This has the disadvantage that during their actuation the mixing piston, the separating piston and the expulsion piston must operate across a joint between the transport cylinders, which represents a discontinuity.

SUMMARY OF THE INVENTION

It is an object of the present invention to provide a reliable and well-functioning transport and processing apparatus.

This object is attained by giving the transport chamber for the liquid component a ring shape with a central aperture and with a membrane; by expelling mixed two-component material through the central aperture and the opening; and by destroying the membrane by a relative movement between the transport chamber for the liquid component and a solid body enclosed in the container in order to effect a flow of the liquid component into the transport chamber for the powder component.

An advantage of this apparatus is that it can be executed without rubber-like soft seals in the form of O-rings or lips. This enables the apparatus to be manufactured of injection molded plastic parts with the exception of a membrane. Furthermore, no collapsed transport containers need be moved along by the expulsion piston during the expulsion of the mixture.

A further advantage of this apparatus is that preassembled injection molded plastic parts can be delivered to a filling establishment and that final assembly, welding in and, where required, sterilization are possible along with the filling. Independently of the transport and storage, filled quantities arrive directly at the place of work along with the apparatus, which is ready for use. The apparatus can be actuated from the outside for the mixing and expulsion of the two components. The inner space can remain closed off until the expulsion.

Through the design of the membrane as a ring-shaped film, the transport chamber for the liquid component can be manufactured in a simple injection molding tool and an attacking force for the destruction of the membrane is effective everywhere on the cross-section of the transport chamber. A filling aperture at the transport chamber for the liquid component which can be closed off from the outside enables the liquid component and the powder component to be filled in in the same vertical position of the container. Through an axial fixing possibility for the mixing piston during the transport and storage, the movement of the mixing piston during mixing can be used for the destruction of the membrane. A displacement member which penetrates into the transport chamber for the liquid component has the advantage that the liquid component is expelled necessarily and independently of the force of gravity. The displacement member can be provided with a cutting edge and can thus destroy the membrane at the beginning of the relative movement between the displacement member and the transport chamber. If the displacement member and the transport chamber also mutually bind with one another at the end of the expulsion movement, this process becomes irreversible and there is no danger of differently mixed portions of the product being thrust back into the transport chamber for the liquid component. By using a hollow piston rod for the mixing piston which has a closure reaching up to the piston, the piston rod can be used as an outlet tube without dead spaces with unequal mixing arising.

Forming the transport chamber for the liquid component as a ring chamber also makes it possible to integrate the transport chamber into a container cover which is axially movable with respect to the container in order to destroy the membrane at a cutting edge of fixed location in the container and in order to allow the liquid component to flow into the transport chamber for the powder component lying beneath it under the action of gravity. Advantageous in this arrangement is a lead-off ring, via which the liquid component flows off, and a draw ring, which latches with the container cover when the latter is first lowered and frees an outflow cross-section when the container cover is lifted. When the container cover is again lowered, this outflow cross-section is closed off again in order to prevent the bone cement from entering into the transport chamber for the liquid component during the subsequent mixing and expulsion of the two components. An axial movement which can be controlled from without can, for example, be produced through a container cover by a rotational movement which is performed spirally with respect to the container.

DESCRIPTION OF THE PREFERRED EMBODIMENTS

The figures show transport and processing apparatuses for a two-component material, in particular for bone cement, having a liquid component and a powder component which are separated by a membrane, and each occupy a transport chamber in a closeable container which has an expulsion piston at the one end and an opening for the expulsion of mixed two-component material at the opposite end. By giving the transport chamber for the liquid component a ring shape with a central aperture, the mixed two-component material can be expelled through the aperture. The membrane is destroyed by a relative movement between the transport chamber for the liquid component and a solid body enclosed in the container in order to effect a flow of the liquid component into the transport chamber for the powder component and to enable the mixing with a mixing piston.

Figure 1:
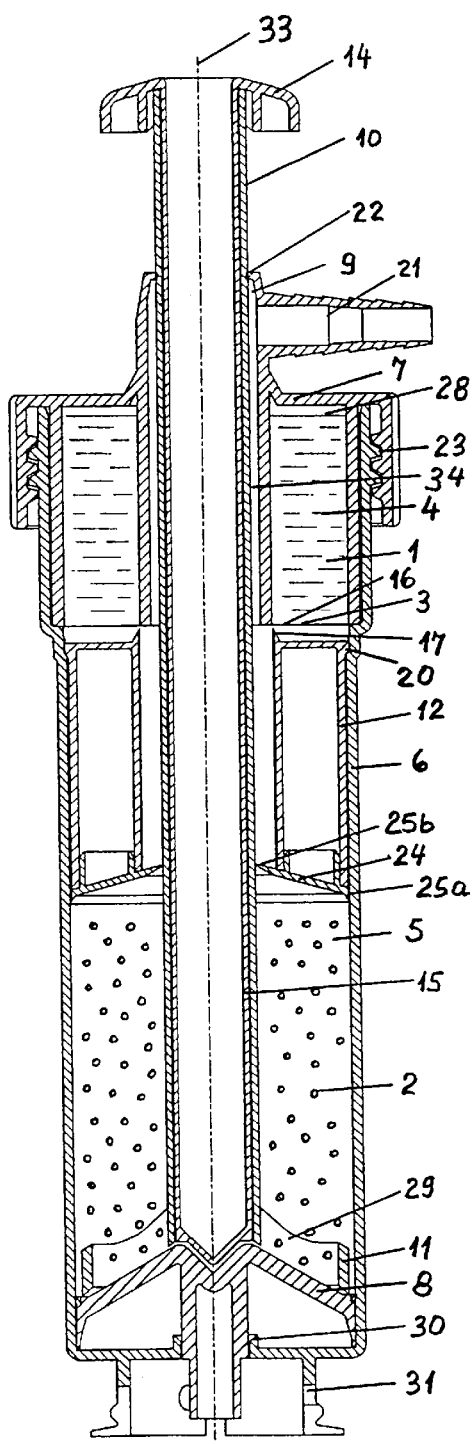
FIG. 1 is a schematic longitudinal section through a filled transport and processing apparatus in which the transport chamber for the liquid component is integrated into the container cover and which has a displacement member.
Figure 2:
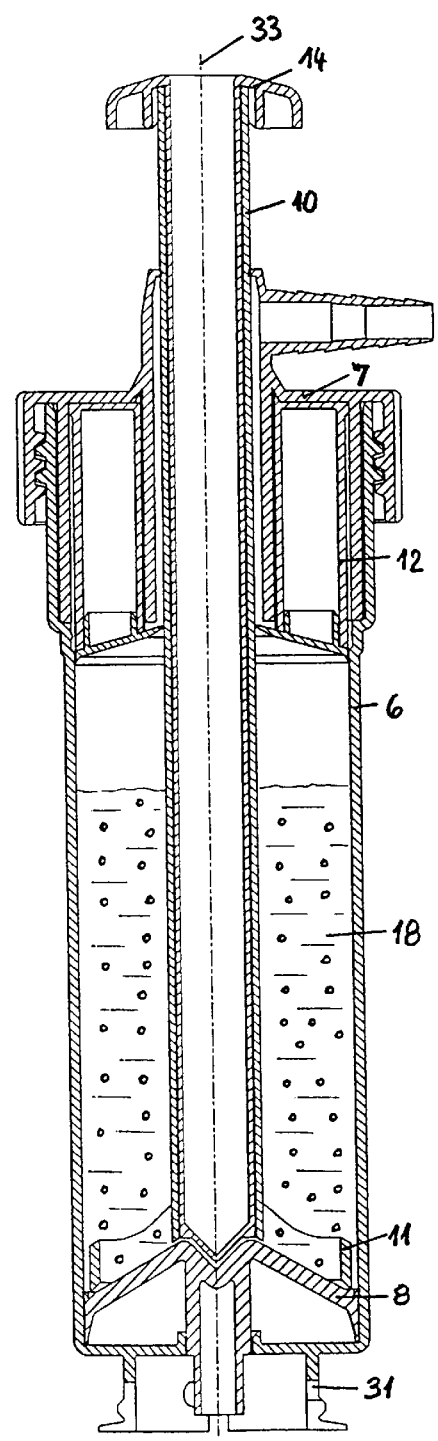
FIG. 2 shows the transport chamber for the liquid component with an inwardly moved and blocked displacement member after the mixing, shown schematically in the longitudinal section of FIG. 1.

In the example of FIGS. 1 and 2 the transport container consists of an actual container 6 and a container cover 7 which is designed as a transport chamber 4 for the liquid component 1, which has the shape of a ring and which is closed off by a membrane 3 in the form of a circular ring film or foil 16. The filling with the liquid component 1 and the sealing off of the transport chamber 4 with the film 16 are done in a preparatory operation. For the further preparation of the apparatus the following steps are taken:

The expulsion piston 8 is pressed in to the cylindrical container 6 and fixed with a snap connection 30;

the mixing piston 11 with the piston rod 10 is placed on the expulsion piston 8;

the powder component 2 is filled in;

the displacement member 12 is inserted into the container 6 and latched, with the displacement member 12 having a cover 24 with two guide lips 25a, b which hold back the powder component 2;

the cover 7 with the liquid component 1 in the transport chamber 4 is passed over the hollow piston rod 10 and secured to the container 6 with a screw connection 23; and a closure 14 in the form of an outwardly bulging knob is inserted into the piston rod and the container 6 is closed, with only a vacuum extraction opening 21 not yet being closed off.

In this state the apparatus is ready for use for the mixing of the two components. In the case of bone cement the apparatus is welded into a film for transport and storage and sterilized with γ-rays or a gas, e.g. ethylene oxide, or formaldehyde. The parts of the apparatus are executed as injection molded parts of plastic and are transparent in order to be able to monitor the mixing at a later time. The sterilization is done either prior to filling using γ-rays or afterwards using gas in order that the liquid is not damaged by γ-rays.

In the case of bone cement, the apparatus is brought into the operating room in a sterile condition. For mixing the following steps are taken:

The mixing piston 11 with the piston rod 10 is pulled out of a transport securing device 22 and through the powder component 2, with the flowable powder flowing past the mixing piston 11 through slits 29;

the displacement member 12 with its cutting edge 17 is torn by the mixing piston 11 out of its snap connection 20 and pressed into the transport chamber 4 of the liquid component, with the cutting edge 17 tearing open the film 16 and the displacement member 12 completely displacing the liquid component 1 into the transport chamber 5 for the powder component;

the displacement member 12 binds in its final position (FIG. 2) in the transport chamber 5 of the liquid component 1 so that only the components 1, 2 and the mixing piston 11 are still mutually movable;

the mixing piston is thrust up and down by a predetermined number of strokes, for example 30 strokes, while being rotated in order to achieve a thorough mixing of the components 1, 2;

a vacuum is applied for a limited time to the vacuum extraction opening in order to suck off vapors and rising air bubbles; and the closure 14 is removed, the mixing piston 11 is held in an upper position and a forward thrust apparatus with a thrust rod is set onto a bayonet connection 31 in order to be able to expel the finished mixture 18 through the hollow piston rod 10 with the expulsion piston 8.

The closure plug 14 and its hand grip can be unscrewed from the piston rod 10. Favorable expulsion shapes result from the fact that most of the parts are made substantially rotationally symmetric with respect to the main axis 33.

Figure 3:
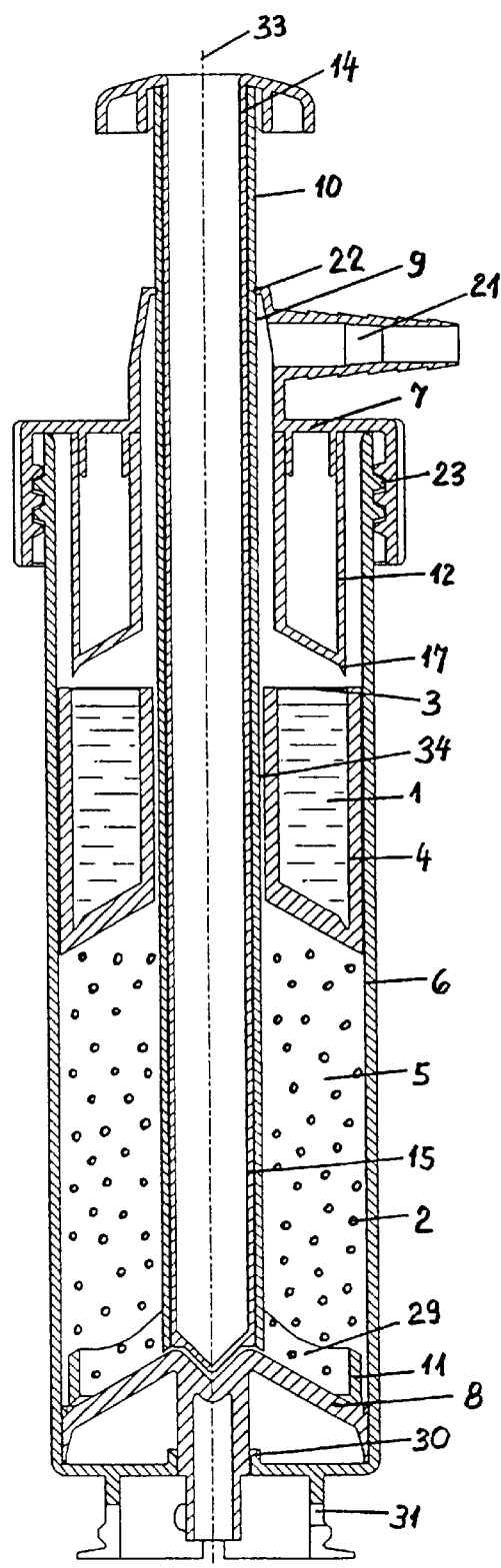
FIG. 3 is a schematic longitudinal section of a filled transport and processing apparatus in which a displacement member is integrated into the container cover, while the transport chamber for the liquid component is fixed in the container as a separate vessel in a transport position.
Figure 4:
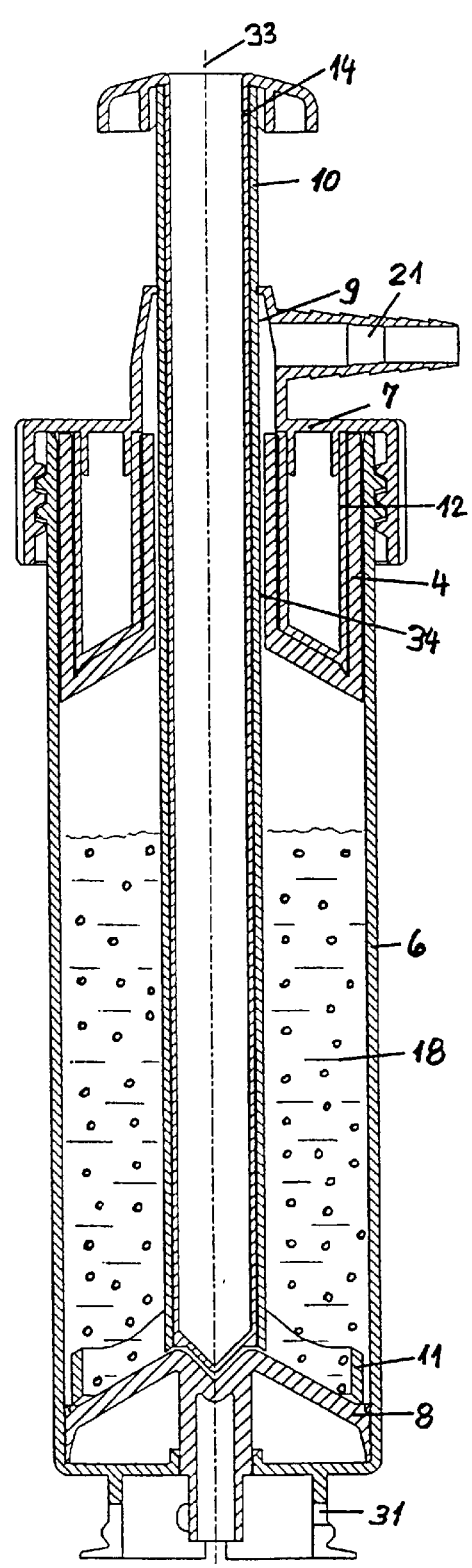
FIG. 4 is the inwardly moved and blocked transport chamber for the liquid component after the mixing shown schematically in the longitudinal section of FIG. 3.
Figure 5:
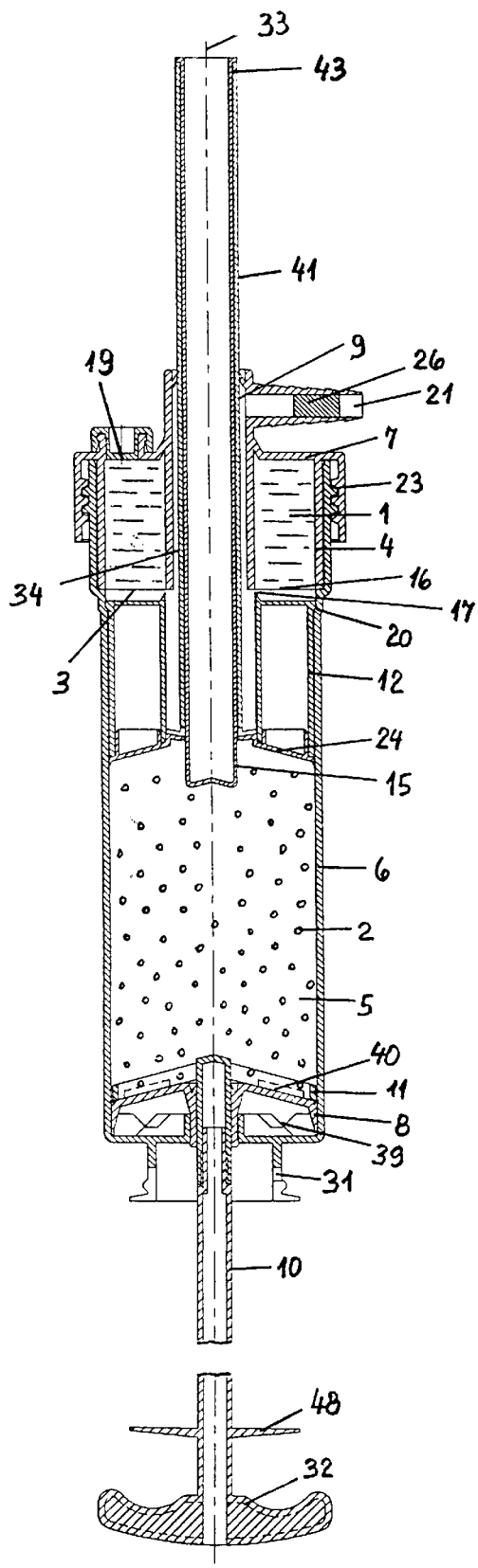
FIG. 5 is a schematic longitudinal section of an arrangement analogous to FIG. 1 in which a mixing piston can be actuated by a piston rod through the expulsion piston.
Figure 6:
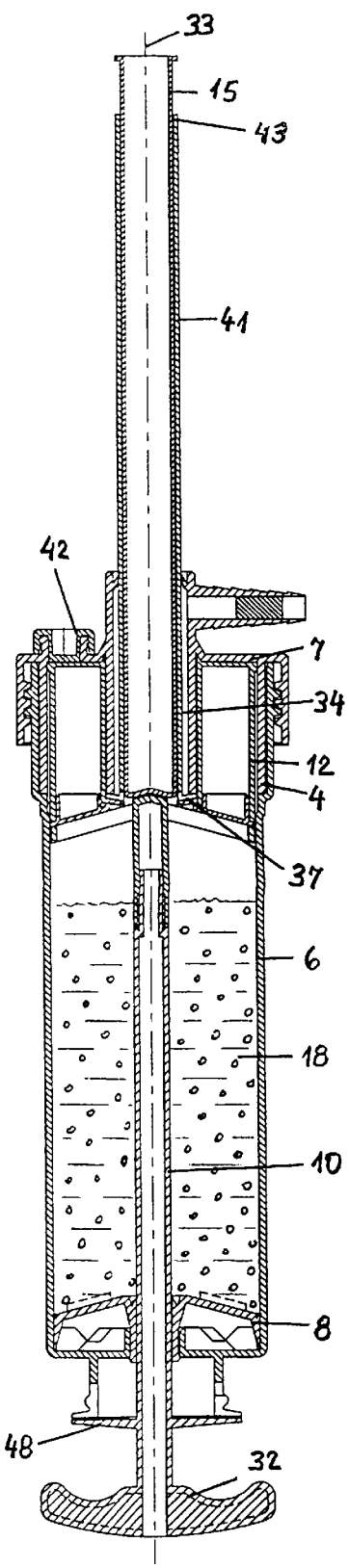
FIG. 6 is the arrangement of FIG. 5 in a schematic longitudinal section after the mixing.

In the example of FIGS. 3, 4 only the arrangement of the displacement member 12 and the transport chamber 4 for the liquid component 1 are exchanged in comparison with the preceding example. The container 6 and the expulsion piston 8 are likewise pre-assembled. The transport chamber 4 for the liquid component 1 is a separate container which is filled with the liquid component 1 and closed with and welded to a film 3. For the filling of the apparatus the mixing piston 11 and the piston rod 10 are inserted in the container 6. Then the powder component 2 is filled in and the ring-shaped transport chamber 4 for the liquid component is pushed over the piston rod 10 and anchored in the container 6. The cover 7 with the integrated displacement member 12 is put on and closes the container 6 with the screw connection 23. Lastly the closure 14, which has a hand grip and a protrusion up to the mixing piston 11, is connected to the tubular piston rod 10 via a thread at the hand grip. The protrusion 15 prevents dead spaces with unequal distribution of the components 1, 2 from arising during the subsequent mixing.

For the actual mixing (FIG. 4) the mixing piston 11 traverses the powder component 2 and thrusts the transport chamber 4 for the liquid component against the cutting edge 17 for the destruction of the membrane 3 and further over the displacement member 12 in order to expel the liquid component 1. In their final positions the displacement member 12 and the transport chamber 4 bind with one another. After the mixing with the mixing piston 11 and the possible extraction of vapors by suction via a suction opening 21 the mixing piston 11 is fixed in an upper position via the piston rod 10 and the closure 14 with the hand grip and the protrusion 15 is removed. After the application of a forward thrust apparatus (not shown here) at the bayonet connection 31 the mixed cement 18 can be expelled through the openings 9, 34, 10 which are concentrically disposed with respect to one another.

Figure 7A:
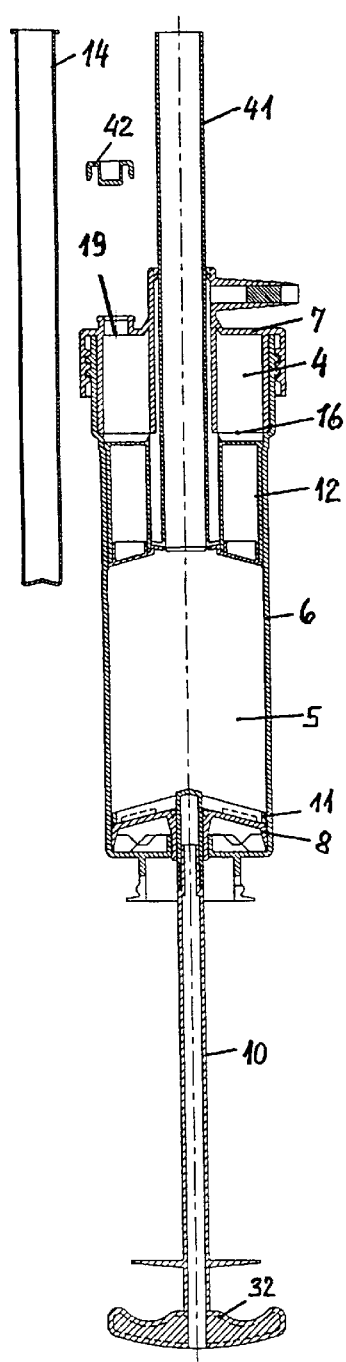
FIGS. 7a, b, c show the filling of the liquid component and of the powder component in an arrangement in accordance with FIG. 5.

A further embodiment is shown in FIGS. 5, 6 and 7a to 7i. The apparatus consists (FIGS. 5, 6) of an arrangement which is concentric to a longitudinal axis 33 with a container 6 which has an opening for a hub of the expulsion piston 8 at its lower end and which can be connected via a bayonet connection 31 to a forward thrust apparatus 27 (FIG. 7i). The container 6 is closed off with a screw connection 23 at its upper end by a cover 7 which has an opening 9 from which a vacuum extraction opening 21 with a filter 26 branches off. At the same time the cover 7 is executed as a transport chamber 4 for the liquid component 1. It is closed off at its lower end by a membrane 3 in the form of a ring-shaped film 16. A non central filling opening 19 which can be closed by a plug 42 is provided at its upper end. A displacement member 12 is connected via a snap connection 20 to the container 6 in a transport position and has an outflow tube 41 which is led out through the opening 9 in the cover 7. The outflow tube 41 can be closed off by a protrusion 15. Outflow apertures 37 are provided at the transition between the outflow tube and the actual displacement member 12 and are freed when a mixing piston 11 reaches the uppermost position with respect to the displacement member 12 and thrusts back the protrusion 15. Constructionally, the outflow tube 41 is a part of a cover 24 which closes off the hollow displacement member 12. In its lower position the mixing piston 11 can be connected to the expulsion piston 8 via a latch 40, with it being possible for the expulsion piston 8 to take up torques in its lower position via a rotational securing device 39 to the container 6. At its hub the expulsion piston 8 has a central bore through which a portion of the piston rod 10 for the mixing piston 11 is led out in the form of a sleeve with a thread. The actual piston rod 10 has a hand grip 32 and an abutment 48. It can be screwed to the mixing piston 11 via a thread.

FIG. 7a shows the apparatus in the pre-assembled state. The expulsion piston 8 is inserted. The mixing piston 11 is latched in the lowest position to the expulsion piston 8 and its piston rod 10 is inserted. The displacement member 12 with the outflow tube 41 is connected to the container 6 in the transport position. The cover 7 is screwed onto the container 6.

Figure 7B:
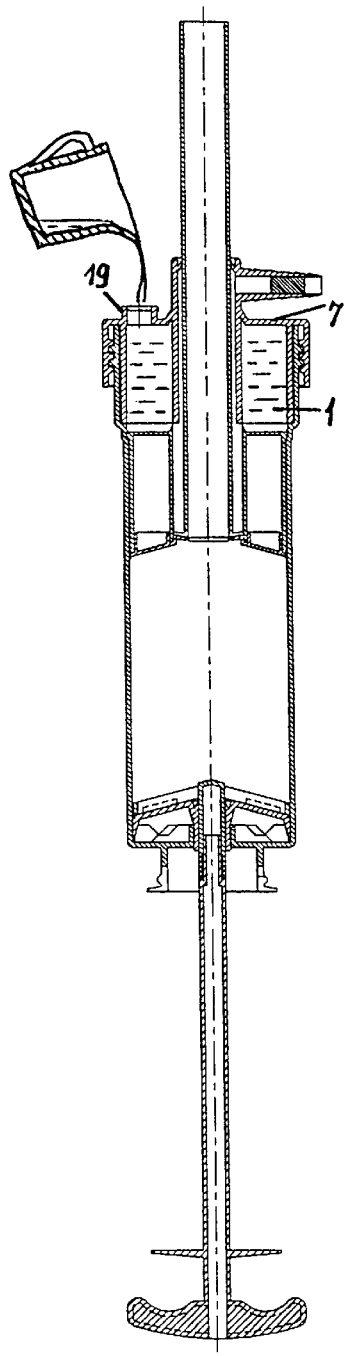
FIG. 7d is a schematic longitudinal section of an arrangement in accordance with FIG. 5 which is filled and ready for use.
FIG. 7e is a schematic longitudinal section in accordance with FIG. 5 of the bringing together of the liquid component and the powder component.
FIG. 7f is a schematic longitudinal section in accordance with FIG. 5 of the mixing of the two components.
FIG. 7g is a schematic longitudinal section in accordance with FIG. 5 of the release of the piston rod from the mixing piston.
FIG. 7h is a schematic longitudinal section in accordance with FIG. 5 of the extraction of the vapors from the container by suction.
FIG. 7i is a schematic longitudinal section in accordance with FIG. 5 of the mixture, which is ready to be expelled, in the container.

In FIG. 7b the liquid component 1 is being filled in through a filling opening 19 in the cover 7 and the filling opening is closed with a plug 42. For large series the filling is done at a filling station with an immersion probe and pre-proportioned amounts of liquid.

Figure 7C:
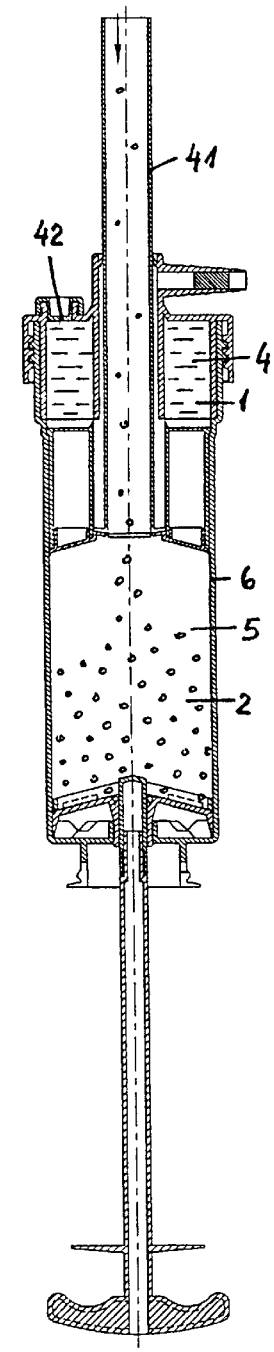

In FIG. 7c the powder component 2 is filled into its transport chamber 5 in the container 6 through the outflow tube 41. In order not to impede the outflow aperture 3 at the displacement member 12 and in order to avoid the development of dust, an immersion probe which projects into the transport chamber 5 during filling is advantageous.

In FIG. 7d the filled container 6 is closed off with the protrusion 15 and can, for example for bone cement, be welded into a film and sterilized in this arrangement. The apparatus can be transported and stored in this arrangement and is ready for operation at any time for a mixing and expulsion of two-component material 1, 2.

For mixing the apparatus is pressed against a counter-surface with the downwardly directed hand grip 32 in order to release the latching 40 between the mixing piston and the expulsion piston. The mixing piston passes through the powder component 2 and encounters the protrusion 15, which is thrust outward to such an extent (FIG. 7e) that the outflow openings 37 for the liquid component 1 are freed. At the same time the displacement member 12 is torn out of its snap connection 20 and destroys the film of the transport chamber 4 of the liquid component with its cutting edge in order to completely displace the liquid component 1. The latter flows through the outflow openings 37 into the transport chamber 5 of the powder component. The displacement member 12 and the outflow tube 41 bind with one another in an uppermost position and the actual thorough mixing (FIG. 7f) can take place. For this, the mixing piston 11 is moved up and down by a predetermined number of strokes while being rotated and the two components are pressed through slits 29 at the mixing piston 11 in the presence of mutual friction.

In FIG. 7g the mixing piston 11 is latched in the lowermost position at the expulsion piston 40 in order to unscrew the piston rod 10 with the hand grip 32 from the mixing piston 11. The counter-torque required for this is transmitted from the container 6 via the rotational securing device 39 to the expulsion piston 8 and from the latter via the latch 40 to the mixing piston.

In FIG. 7h a hose is attached to the vacuum extraction opening 21 for sucking off solvent vapors, with a filter 26 preventing an intrusion of solid or highly viscous particles.

In FIG. 7i a forward thrust apparatus 27 (which is not shown further) is attached to the bayonet connection 31. This acts on the expulsion piston 8 with a thrust rod 44. As soon as the protrusion 15 has been completely removed, the still liquid cement can be expelled from the outflow tube 41 via an opening 43.

Figure 8:
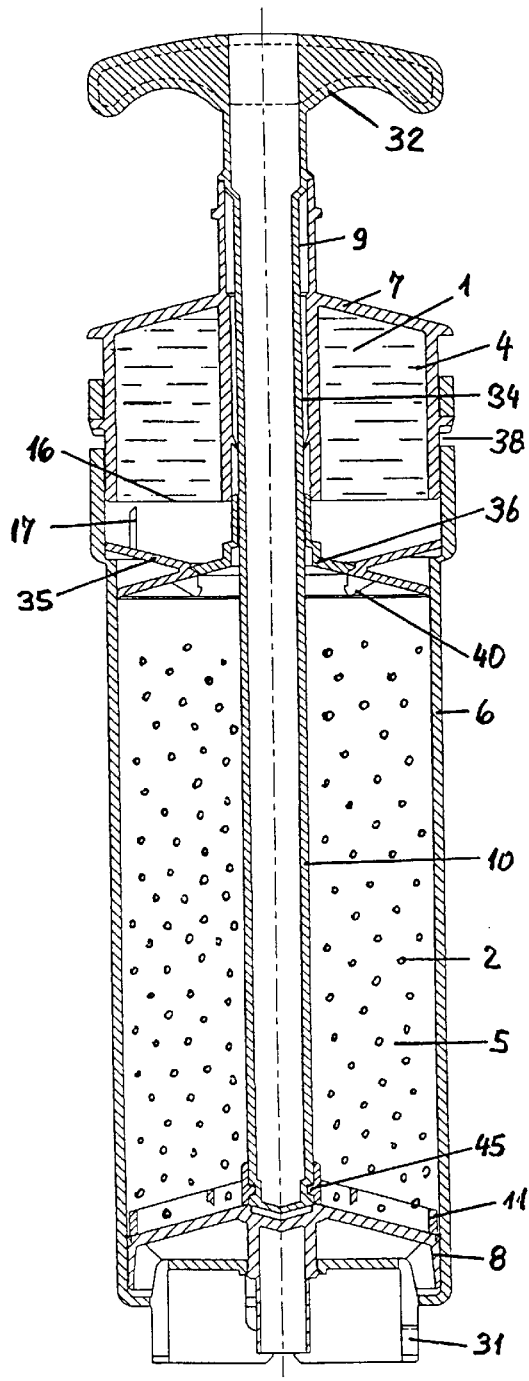
FIG. 8 is a schematic longitudinal section of a transport and mixing apparatus with an axially movable cover, which contains the liquid component, in the transport position.

A further embodiment is shown in FIGS. 8, 9 and 10a to j. FIG. 8 illustrates an apparatus which is ready for use. The container 6 is closed off at the lower side by the expulsion piston 8, on which the mixing piston 11 lies. The mixing piston 11 is actuated via a piston rod 10 which has a releasable connection 45 to the mixing piston 11 and which is led upwardly out of the container cover 7 and terminates in a hand grip 32. The transport chamber 5 for the powder component 2 is closed off upwardly by a lead-off ring 35 which is pressed in and by a draw-ring 36. At the spatially fixed lead-off ring 35 several, for example, four, cutting edges 17 and a latch 40 for the mixing piston 11 are provided. The draw ring 36 can be moved in the axial direction only by overcoming a clamping force. It binds with its uppermost position in the cover 7 and can then be moved only together with the cover. The cover 7 has a central aperture 34, through which the piston rod 10 can be pushed in and drawn out. After the mixing and the drawing out of the piston rod the cement can be expelled through this central aperture 34 and the opening 9 adjoining thereto. The cover 7 is designed as a ring-shaped transport chamber 4 for the liquid component 1 and is closed off at its lower end by a film 16. The cover is journalled in the radial direction in recesses in the form of a helix 38 and can be rotated forwards and backwards by about 60° with respect to the container 6, wherein it executes a stroke of about 6 mm.

Figure 9:
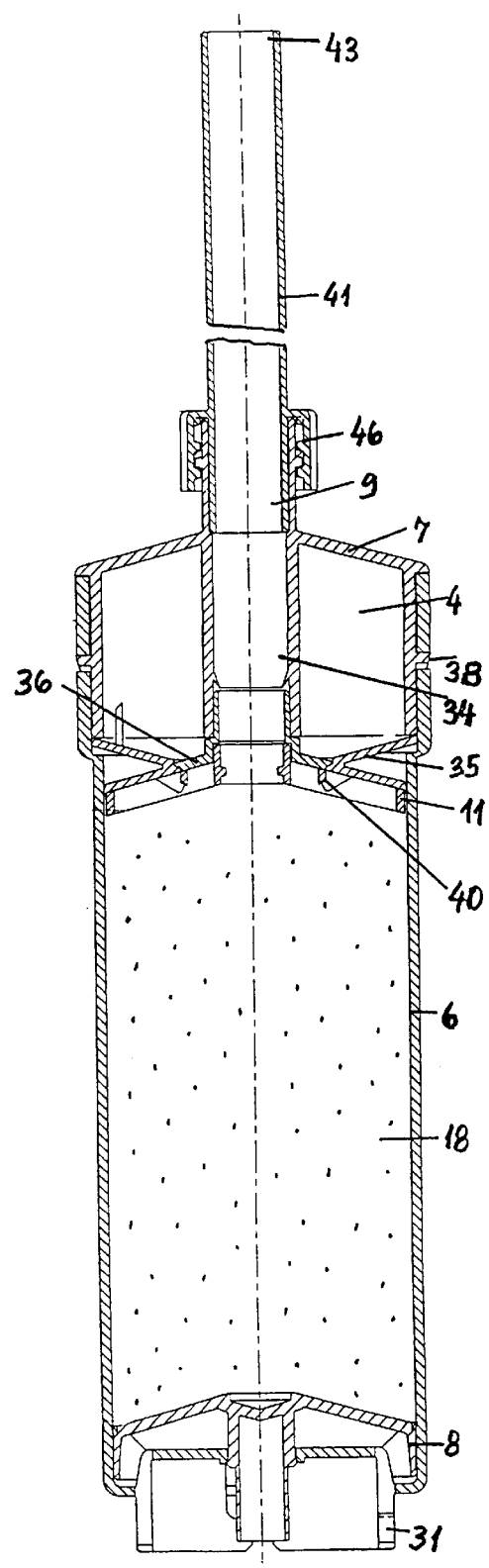
FIG. 9 a schematic longitudinal section of the apparatus of FIG. 8 after the mixing of the components, with the piston rod already having been removed from the mixing piston and an expulsion tube having been put on in its place.

In FIG. 9 the cement has already been mixed. The mixing piston 11 is connected in its uppermost position to the lead-off ring 35 via the latch 40. The piston rod 10 has been drawn out by releasing the connection 45, and in its place an outflow tube 41 with the opening 43 is attached to the cover 7 via a connector 46. The cover 7 is located in its lower position with respect to the container 6 and secures the draw-ring 36.

Figure 10E:
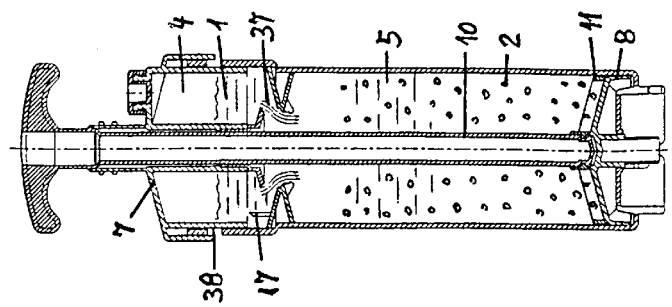
FIGS. 10e, f, g, h, i, j show the bringing together and mixing of the components, the extraction of solvent vapors by suction, and an apparatus, which is ready for expulsion, with an expulsion tube pushed on, shown schematically in the longitudinal section of FIG. 8.
Figure 10D:
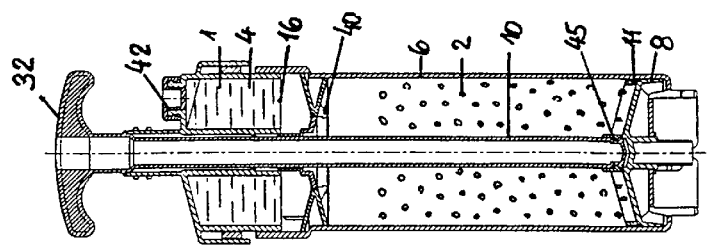
FIG. 10d is a schematic longitudinal section of an apparatus in accordance with FIG. 8 which is ready for use.
Figure 10C:
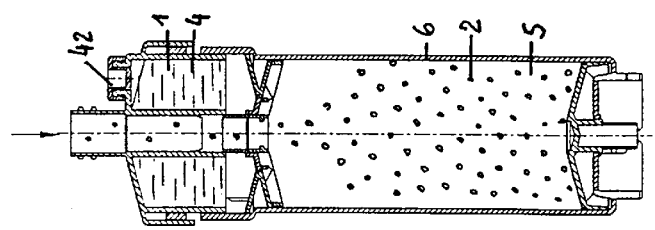
FIGS. 10a, b, c are schematic longitudinal sections of the filling of the components into an apparatus in accordance with FIG. 8.
Figure 10B:
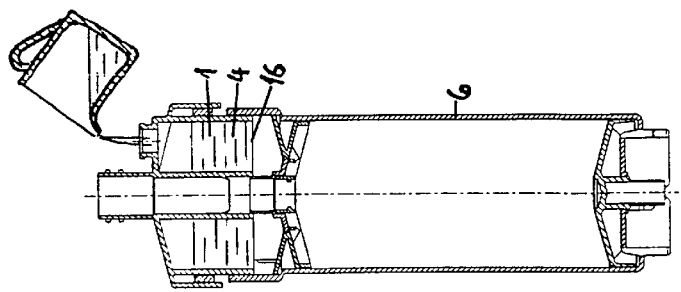
Figure 10A:
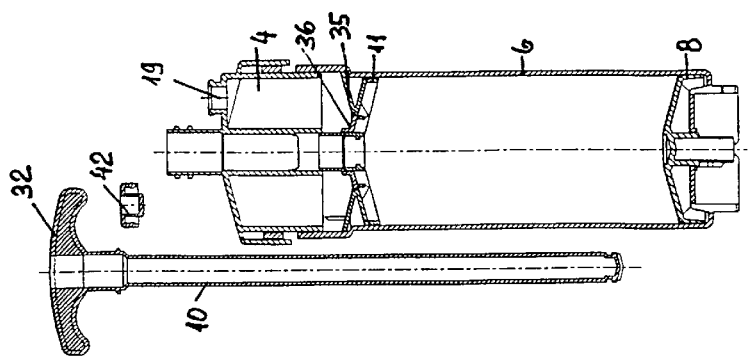

FIG. 10a shows the state of the apparatus as delivered prior to filling. The expulsion piston 8 is inserted in the container 6. Likewise the lead-off ring 35 with the latched mixing piston 11 has been pressed in with a metered force on a press. The cover 7 has already been sealed with a film and pushed on with the inserted draw-ring 36 in its uppermost position with respect to the container 6 and still has an opening 19 for filling. The closure plug 42 and the piston rod 10 with a hand grip 32 are included separately in the delivery.

In FIG. 10b the liquid component 1 is filled into its transport chamber 4. A filling probe is also of advantage here, however it must not damage the closure film 16.

In FIG. 10c the transport chamber 4 for the liquid component 1 is already closed off by the plug 42 and the transport chamber 5 of the powder component 2 is being filled up. Here as well, an immersion probe is of advantage for the filling process.

In FIG. 10d the piston rod 10 is inserted from above into the filled container 6 and connected at its lowest position via a collar to the container cover 7. During the downward movement the mixing piston 11 is released from its latch 40 and moved along. At the same time a releasable connection 45 to the piston rod 10 is established. The apparatus would now be ready for use for the mixing and can be stored and transported in this form.

In FIG. 10e the liquid component 1 is released by a first forward rotation and an immediately following backward rotation of the cover 7. During the forward rotation along the helix 38, the transport chamber 4 with the film 16 dips into the cutting edges 17 and is torn open. At the same time the cover 7 is pushed onto the draw-ring and holds the latter fast. During the immediately following backward rotation, the cover 7 lifts the draw-ring and frees a ring-shaped outflow opening 37 for the liquid component, which now flows out into the transport chamber 5 of the powder component 2 under the action of gravity. After the liquid component has completely flowed out, which can be determined when the container cover 7 is transparent, a second forward rotation of the cover 7 is performed which presses the draw-ring 36 against the lead-off ring 35 and thus encloses both components 1, 2 in the transport chamber 5 of the powder component 2 for mixing (FIG. 10f).

In FIG. 10g the actual mixing takes place via the hand grip 32, the piston rod 10 and the mixing piston 11. After the prescribed stroke movements have been completed, the piston rod 10 is drawn all the way up (FIG. 10h). The mixing piston 11 again moves into the latch 40 at the lead-off ring 35 and the piston rod 10 is released from its connection 45 at the mixing piston 11. Optionally, a vacuum extraction tube 47 can subsequently be placed on the cover 7 (FIG. 10i) in order to suck off solvent vapors and air bubbles from the mixed cement 18.

In FIG. 10j an outflow tube 41 with a connector 46 is mounted in place of the vacuuming tube 47. A forward thrust apparatus 27 which can expel the cement with a thrust rod 44 via an opening 43 at the outflow tube 41 is secured to the lower end of the container.

What is claimed is:

1. Transport and processing apparatus for a two-component material having a liquid component and a powder component which are separated by a membrane and each occupy a transport chamber in a closeable container which has an expulsion piston at one end and an opening for the expulsion of mixed two-component material at an opposite end and which encloses a perforated mixing piston, the transport chamber for the liquid component being executed in ring shape with a central aperture and a membrane, wherein the mixed two-component material can be expelled through a central aperture and an opening; and wherein the membrane can be destroyed by a relative movement between the transport chamber for the liquid component and a solid body enclosed in the container in order to effect a flow of the liquid component into the transport chamber for the powder component.

2. Apparatus in accordance with claim 1, wherein the membrane is formed by a ring-shaped film.

3. Apparatus in accordance with claim 1 wherein the transport chamber for the liquid component has in addition to the membrane a further filling opening which can be closed off from the outside.

4. Apparatus in accordance with claim 1, wherein the mixing piston can be fixed axially in at least one position.

5. Apparatus in accordance with claim 1, wherein a displacement member is enclosed in the container and experiences a relative movement with respect to the transport chamber for the liquid component through the mixing piston in order to destroy the membrane and to displace the liquid component out of its transport chamber.

6. Apparatus in accordance with claim 5 wherein the displacement member and the transport chamber for the liquid component bind with one another at the end of the expulsion of the liquid component.

7. Apparatus in accordance with claim 1 wherein the mixing piston has a piston rod which leads through the opening, is made hollow as an outlet tube, and has a closure.

8. Apparatus in accordance with claim 7 wherein a closure with a protrusion fills out the hollow piston rod up to the mixing piston for preventing an intrusion of the powder component prior to and during the mixing.

9. Apparatus in accordance with claim 5 wherein the displacement member has a cutting edge for destroying the membrane.

10. Apparatus in accordance with claim 1 wherein the transport chamber for the liquid component is integrated as a ring chamber into a container cover of the container.

11. Apparatus in accordance with claim 5 wherein the displacement member can be displaced by the mixing piston as an axially movable ring.

12. Apparatus in accordance with claim 5 wherein chamber for the liquid component can be displaced in the container as an axially movable ring, and wherein the displacement member is integrated into the container cover at a fixed location.

13. Apparatus in accordance with claim 11 wherein the movable ring is held in a transport position in the container with a snap connection for preventing unintentional damage to the membrane.

14. Apparatus in accordance with claim 10 wherein the container cover with the transport chamber for the liquid component is movable in the axial direction with respect to the container for destroying the membrane with a cutting edge at a fixed location.

15. Apparatus in accordance with claim 14 wherein between the cutting edge and the transport chamber for the powder component a fixed lead off ring and a draw-ring which is axially movable under a bias force with respect to the container cover are arranged, said rings keeping the powder component away from the region of the cutting edge during transport and storage of the material to be mixed away from the cutting edge during the mixing process, the membrane running into the cutting edge during the first axial lowering of the container cover and the draw ring being latched together with the container cover for providing an outlet opening for the liquid component when the container cover is drawn back, and wherein said opening can be closed off again for mixing by a second axial lowering of the container cover.

16. Apparatus in accordance with claim 15 wherein the axial movement between the container cover and the container is produced by rotation via a spiral.

17. Apparatus in accordance with claim 1 wherein the container has a vacuum extraction opening for sucking off vapors.

18. Method for the mixing and compressing of a two-component material with a transport and processing apparatus for the two-component material having a liquid component and a powder component which are separated by a membrane and which each occupy a transport chamber in a closeable container having an expulsion piston at one end and an opening for the expulsion of mixed two-component material at an opposite end and which encloses a perforated mixing piston, the transport chamber for the liquid component defining a ring shape with a central aperture and a membrane, the mixed two-component material being expellable through a central aperture and an opening, the membrane being destroyed by relative movement between the transport chamber for the liquid component and a solid body enclosed in the container to effect a flow of the liquid component into the transport chamber for the powder component, the method comprising the steps of moving the enclosed solid body out of a transport position relative to the transport chamber for the liquid component to such an extent that the membrane is destroyed, moving the mixing piston up and down over a predetermined number of strokes, sucking off solvent vapors from the transport chambers, and opening the expulsion opening and actuating the expulsion piston in order to expel the mixture.

19. Method in accordance with claim 18 including the steps of inserting the expulsion piston into the container, inserting the mixing piston into the container, enclosing the liquid component in a ring-shaped transport chamber provided with a membrane, enclosing the transport chamber for the liquid component in the container, introducing the powder component into the container, introducing the solid body into the container, closing the container cover at its expulsion opening, and welding the apparatus into a transport and storage film while it is in a sterile atmosphere.

* * * * *